United States Patent
Gelbfish

[11] Patent Number: 6,059,745
[45] Date of Patent: May 9, 2000

[54] THROMBECTOMY DEVICE AND ASSOCIATED METHOD

[76] Inventor: Gary A. Gelbfish, 2502 Ave. I, Brooklyn, N.Y. 11210

[21] Appl. No.: 08/858,938

[22] Filed: May 20, 1997

[51] Int. Cl.$^7$ .................................................... A61M 1/34
[52] U.S. Cl. .................................. 604/5; 604/9; 606/200
[58] Field of Search ................................ 604/9, 10, 7, 4, 604/5, 6; 606/200

[56] References Cited

U.S. PATENT DOCUMENTS

| | | |
|---|---|---|
| 1,599,741 | 9/1926 | Billings .......................................... 604/7 |
| 1,845,479 | 2/1932 | Carpenter ...................................... 604/7 |
| 3,853,126 | 12/1974 | Schulte . |
| 3,882,862 | 5/1975 | Berend . |
| 3,993,067 | 11/1976 | Schachet ...................................... 604/9 |
| 4,560,375 | 12/1985 | Schulte et al. . |
| 4,586,919 | 5/1986 | Taheri . |
| 4,741,730 | 5/1988 | Dormandy, Jr. et al. . |
| 4,767,399 | 8/1988 | Bollish . |

FOREIGN PATENT DOCUMENTS 369126  8/1921  Germany ..................................... 604/7

*Primary Examiner*—Michael H. Thaler
*Attorney, Agent, or Firm*—R. Neil Sudol; Henry D. Coleman

[57] ABSTRACT

A thrombectomy device includes a tubular shunt generally connected at an upstream end to a relatively high-pressure blood vessel such as an artery and at a downstream end to a relatively low-pressure blood vessel such as a vein. During use, the shunt is disposed mostly outside of the patient. A filter is disposed in the shunt for blocking the passage of clot particles. This device enables a real-time return of blood to the vascular system of the patient. A selectively operable syringe is operatively connected to the tubular member for exerting an auxiliary force on clot material stuck in one of the tubular member and the inlet port element. A three-way valve element is operable in first configuration to couple the suction device to the inlet port element, in a second configuration to couple the suction device to the outlet port element, and in a third configuration to couple the inlet port element and the outlet port element to one another.

20 Claims, 1 Drawing Sheet

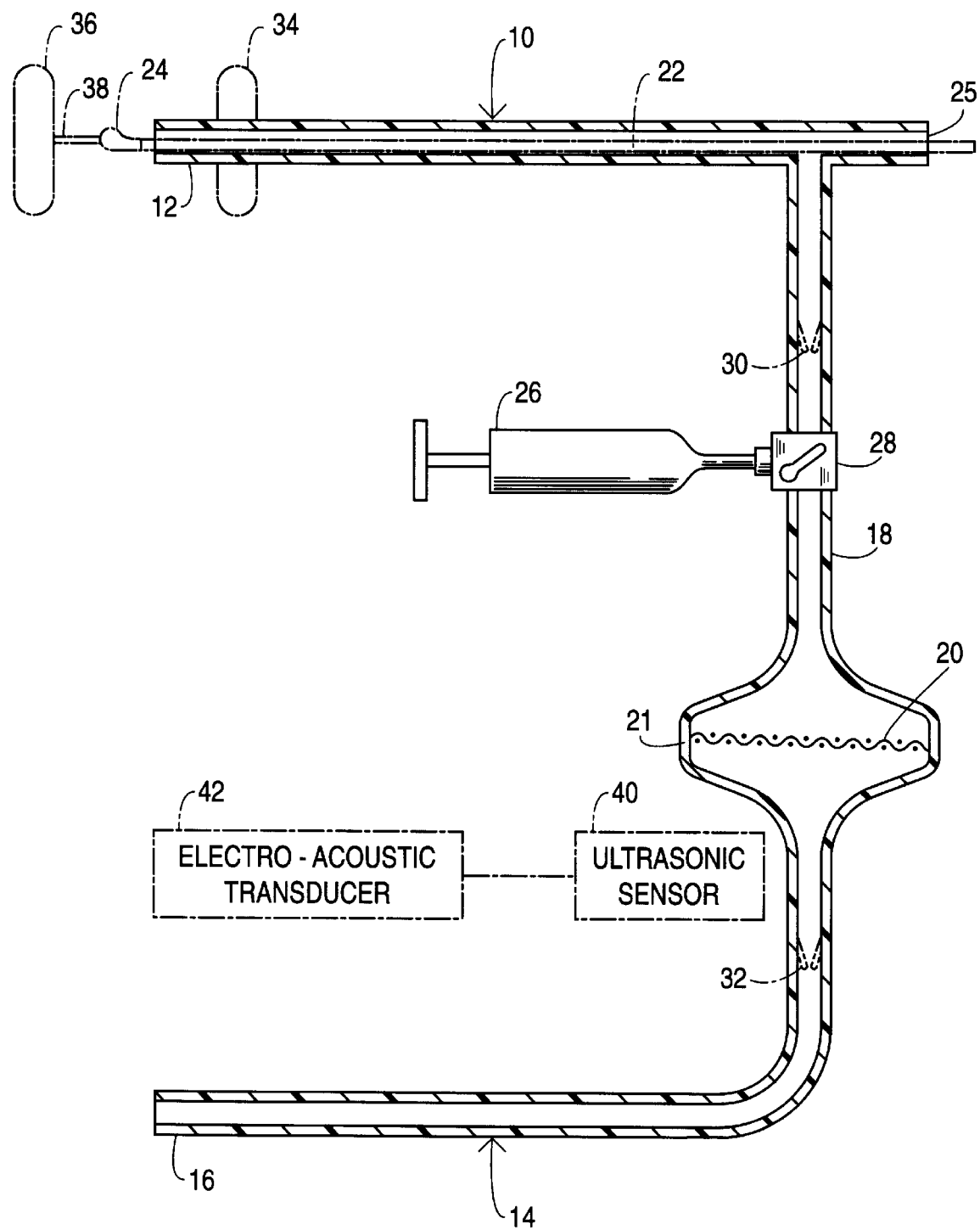

THROMBECTOMY DEVICE AND ASSOCIATED METHOD

BACKGROUND OF THE INVENTION

This invention relates to a thrombectomy device. This invention also relates to an associated method for performing a thrombectomy.

The presence of clot within the human vascular system is always abnormal. It is the cause of significant medical disease. In the arterial system, it can lead to an inability for blood to perfuse and nourish the target tissues with oxygen, a condition known as ischemia. In the venous system, clot can obstruct the drainage pathways, leading to poor blood drainage back to the heart and a buildup in back pressure. This condition is known as venous stasis and venous hypertension, respectively and may cause significant damage to the affected tissues. In some cases, venous clot may also break off and travel to the heart and lungs. This condition is known as pulmonary embolism and is often fatal.

Because of the above-discussed deleterious effects of vascular clot, when such clot is discovered, a treatment modality is almost always undertaken. Several options are available: 1) the patient may be placed on blood-thinning medications (heparin or coumadin) to help dissolve the clot, 2) surgical intervention may be used to remove the clot, or 3) catheters may be inserted through the skin and directed into the affected vessel, with aid of real-time x-ray fluoroscopy. In the last case, several additional options are available. First, clot dissolving enzymes may be infused through the catheter. This technique, however, is time-consuming and the enzymes are expensive. Second, suction may be used to aspirate clot. Lastly, miniaturized blades, rotors, water jets may be used to break up the clot into smaller pieces. This process is beneficial since small fragments are better tolerated by the body and/or they are easier to aspirate via suction without frequent catheter clogging.

Any time suction is used as a primary of secondary method to remove clot, however, blood loss is a real concern. Clot is frequently surrounded by flowing unclotted blood. There is no known way to selectively aspirate only clot and exclude the unwanted blood. To the contrary, suction will preferentially aspirate blood since it is liquid and flowing. Attempts to "latch on" to clot fragments via sudden suction are usually only partly successful and even so, large amounts of blood may be lost in the process.

Depending on multiple factors, including the vascular pressure, flow rates, the configuration of the native vessel and the clot, etc., it may be necessary to aspirate blood volumes that are several orders of magnitude greater than the clot volumes removed. Since any blood loss is undesirable and only several hundred cc's of blood may be aspirated from an adult at a given time without causing death, inadvertent yet obligatory blood loss is often the limiting factor in the ability to continue and complete the aspiration of visualized clot.

OBJECTS OF THE INVENTION

An object of the present invention is to provide a device and/or an associated method for extracting thrombus from a blood vessel of a patient which results in a minimal amount of blood loss to the patient.

Another object of the present invention is to provide such a device and/or method which is simple and easy to effectuate.

It is a further object of the present invention to provide such a device and/or method which is inexpensive and thus cost effective.

It is a more specific object of the present invention to provide such a device and/or method which is manually operable and thus does not require artificial power sources.

An additional specific object of the present invention is to provide such a device and/or method which uses the patient's heart to supply the motive force for clot extraction.

Yet another specific object of the present invention is to provide a device and/or method which is compatible and useful as an accessory for clot removal when used with other clot maceration devices.

It is to be understood that the foregoing objects are generally mutually exclusive and optional. A device or method in accordance with the invention may attain any one or more of the above objects or even other objects not listed above, depending on how the device or method is specifically used. The above and other objects of the present invention will be apparent from the descriptions and drawings herein.

SUMMARY OF THE INVENTION

The invention is directed basically to a thrombectomy device including a tubular shunt generally connected at an upstream end to a relatively high-pressure blood vessel such as an artery and at a downstream end to a relatively low-pressure blood vessel such as a vein. During use, the shunt is disposed mostly outside of the patient. A filter is disposed in the shunt for blocking the passage of clot particles. This invention enables a real-time return of blood to the vascular system of the patient.

It is to be noted that a thrombectomy device in accordance with the present invention may be connected between virtually any two points in a patient's vascular system, regardless of the relative pressures at the two points. In particular, a thrombectomy device in accordance with the present invention may be connected at an inlet end and an outlet end to the same blood vessel, preferably at interspaced points.

In the event that the thrombectomy device is connected between a low pressure blood vessel at an upstream end and a high pressure blood vessel at a downstream end, a pump element such as a manually operable syringe may be used to move the blood and clot material through the thrombectomy device in opposition to the natural vascular pressure differential.

A thrombectomy device comprises, in accordance with the present invention, a tubular member defining a flow path and a clot filter disposed in the tubular member and extending transversely to the flow path for removing clot material from blood flowing along the flow path. An inlet port element is disposed on the tubular member for coupling an inlet end of the tubular member to a blood vessel of a patient wherein clot material is located, while an outlet port element is provided on the tubular member for coupling an outlet end of the tubular member to a different point in the patient's vascular system. The port elements may be integrally formed with the tubular member or attached to the tubular member in a fluid tight seal.

Where a thrombectomy device in accordance with the present invention is connected between a relatively high pressure blood vessel at the upstream or inlet end of the device and a relatively low pressure blood vessel at the downstream or outlet end of the device, a natural pressure differential of the body may provide a principal motive force for clot extraction. More specifically, the pressure generated by cardiac action pushes the clot from the affected blood vessel. Of course, it will appreciated that in some cases an additional force will be necessary such as in cases where a "return" vessel with a lower pressure is not available and blood must be pushed upstream towards a higher-pressure vessel or, for example, to remove clot which becomes stuck in the clot-extraction flow path upstream of the filter. To that end, the device further comprises a selectively operable clot clearance component operatively connected to the tubular member for exerting an auxiliary force on clot material stuck in one of the tubular member and the inlet port element. The auxiliary force tends to move the clot material along the flow path towards the filter. Where the device is connected between a relatively high-pressure blood vessel at an upstream end and a relatively low-pressure blood vessel at a downstream end, the auxiliary force is exerted in addition to a pressure differential between blood in the first blood vessel and blood in the second blood vessel. Where the device is connected between a relatively low-pressure blood vessel at an upstream end and a relatively high-pressure blood vessel at a downstream end, the auxiliary force is exerted in opposition to a pressure differential between blood in the downstream, return vessel and the upstream, clot-containing vessel.

Preferably, the clot clearance component includes a suction device such as a manually operable syringe. The clot clearance component may also include a three-way valve element operable in first configuration to couple the suction device to the inlet port element, in a second configuration to couple the suction device to the outlet port element, and in a third configuration to couple the inlet port element and the outlet port element to one another. Where a natural pressure differential between the upstream blood vessel and the downstream blood vessel provides a motive force for clot extraction, the third configuration of the three-way valve is generally used. However, when clot becomes stuck in the flow path upstream of the filter, the three-way valve is operated to connect the suction device to the inlet port element and to block communication between the inlet port element and the outlet port element. The suction device is then used to apply an extraction force to the stuck clot material. Subsequently, the three-way valve is actuated to connect the suction device to the outlet port element while the flow path between the inlet port element and the outlet port element continues to be blocked. Blood removed from the flow path during the suction procedure is then immediately returned to the patient via the outlet port element. After clearance of the flow path, the three-way valve is operated to reconnect the inlet port to the outlet port and thereby restore the normal flow path. In cases where a significant amount of clot debris has been aspirated into the syringe, it may be disconnected and the contents discarded. Additional valves and fluid paths may be designed to facilitate this process of being able to discard unwanted clot or blood through attached waste tubing yet without disconnecting the syringe or other suction source.

The clot clearance component, particularly including the suction device and the three-way valve may be connected to the tubular member either upstream or downstream of the filter.

According to another feature of the present invention, a cutter element is insertable into the first port element for severing clot pieces from a clot mass. Generally, the cutter element is disposed at a distal end of the inlet port element to effectuate clot cutting at that location. The cutting element may take the form of the tapered cutting element described and claimed in allowed U.S. patent application Ser. No. 08/654,834 filed May 29, 1996, now U.S. Pat. No. 5,662,603. The cutting element may optionally include an integral flushing mechanism as disclosed in that patent application.

To facilitate the directing of clot material in a blood vessel to the distal end of the inlet port element, an inflatable balloon may be disposed at the distal end of the inlet port element. The balloon, when inflated, serves to block flow along the blood vessel and thereby force blood and clot material into the inlet port element for filtering by the device of the invention. This balloon may be one of two balloons, one of the balloons being disposed around the inlet port element at the distal end thereof, the other of the balloons being attached to a catheter inserted through the first port element. The direction of insertion of the inlet port element into the blood vessel, relative to the direction of blood flow therealong, basically determines which of the two balloons is used. On the one hand, where the inlet port element is inserted against the flow of blood, the balloon attached as a cuff on the inlet port element is inflated while the other balloon is not deployed or is maintained in an unexpanded configuration. On the other hand, where the inlet port element is inserted in the direction of blood flow, the balloon on the catheter is inflated while the balloon on the inlet port element is kept in a deflated condition. Other configurations and cycles can be envisioned. For example, even where the inlet port element is inserted in the direction of blood flow, the balloon on the inlet port element can be inflated. When this is done, a reversal of blood flow secondary to flow through the collateral vessels can be used at times to carry the clot debris to the inlet port element.

A method for performing a thrombectomy comprises, in accordance with the present invention, connecting an inlet end of a tubular member to a blood vessel of a patient, where the blood vessel contains clot material to be extracted. An outlet end of the tubular member is connected to the vascular system of the patient, generally at a point spaced from the location of the inlet end of the tubular member in the clot-containing blood vessel. Blood is then guided from the blood vessel through the tubular member to the patient's vascular system. During that passage of blood through the tubular member, clot material carried with the blood from the clot-containing blood vessel is captured by a filter element disposed in the tubular member.

Although it is known to connect a tubular shunt between an artery and a vein of a patient for hemodialysis purposes, it is unknown to connect a shunt with a clot filter between an artery containing thrombus and a vein or between two veins that may have a difference in pressures. A hemodialysis shunt would not be connected to a clot filled artery because that would impair, if not prevent, hemodialysis.

As discussed above, where the inlet end of the tubular thrombectomy member is at a higher vascular pressure point that the outlet end, the natural pressure differential between the upstream and downstream points of connection of the thrombectomy device to the vascular system of the patient is considered sufficient to drive clot material through the device to the filter.

The method in accordance with the present invention may further comprise exerting an auxiliary force on clot material stuck along a flow path between the clot-containing blood vessel and the filter element, thereby moving the clot material along the flow path to the filter element. This auxiliary force is usually exerted in addition to a pressure differential between blood in the clot-containing blood vessel and blood in a second blood vessel. The auxiliary force may be exerted by the application of suction, for example, through the operation of a syringe.

The method advantageously includes closing communication between the clot-containing blood vessel and the downstream blood vessel through the tubular member prior to the exerting of the auxiliary force. This closure between the inlet end and the outlet end of the thrombectomy device may be implemented by operating a three-way valve.

As discussed above, a cutter element may be operated to sever clot pieces from a clot mass inside the clot-containing blood vessel. The severed clot pieces are fed through the tubular member to the filter element. In addition, a balloon may be inflated inside the clot-containing blood vessel upon connection of the inlet end to that blood vessel and the outlet end to another location of the vascular system of the patient, thereby blocking flow of blood along the blood vessel and forcing blood and clot material into the inlet end.

A thrombectomy device and method in accordance with the present invention results in a minimal amount of blood loss to the patient. Any blood removed from the patient is immediately returned, in a real time feed back loop. The thrombectomy method is simple and easy to effectuate. The thrombectomy device is inexpensive and thus cost effective. The device is manually operable and thus does not require artificial power sources. It is also compatible with other devices that macerate clot but rely on suction means to remove the resulting debris.

BRIEF DESCRIPTION OF THE DRAWING

The sole FIGURE of the drawing is a schematic longitudinal cross-sectional view through a thrombectomy device in accordance with the invention.

DESCRIPTION OF THE PREFERRED EMBODIMENTS

As shown in the drawing, a thrombectomy device for treating a patient with a blood vessel containing clot material includes, at an upstream side, a tubular inlet port element 10 which has an inlet or distal end 12 insertable into the thrombus-containing blood vessel. The device further includes, on a downstream side, a tubular outlet port element 14 which has an outlet or distal end 16 also insertable into the patient's vascular system, particularly into a vein. Upstream section or inlet port element 10 and downstream section or outlet port element 14 are connected to one another by a tubular middle section 18 which is provided with a filter screen 20. Filter screen 20 is more particularly located in an expanded portion 21 of tubular middle section 18.

Upon insertion of ends 12 and 16 into an artery and vein, respectively, blood flows along a path (not separately designated) through the device from inlet end 12 to outlet end 16 because of a natural differential between arterial pressure and venous pressure. Generally, the blood flow through the thrombectomy device will pulsate owing to the difference between systolic and diastolic pressures. Any clot material in the flowing blood will be captured or blocked by the filter screen 20.

A cutter member 22 with a tapered head 24 is insertable into upstream section or inlet port element 10 through an ancillary opening 25. Cutter member 22 is used to cut up any clot material which is too large to pass into the inlet end 12. Cutter head 24 may take the form of the tapered cutting element with or without an irrigation capability, as described and claimed in allowed U.S. patent application Ser. No. 08/654,834 filed May 29, 1996, now U.S. Pat. No. 5,662,603, the disclosure of which is hereby incorporated by reference. Opening 25 is covered with a seal (not illustrated), such as a self-sealing membrane traversable by cutter member 22 only, to prevent blood from exiting the thrombectomy device at that point.

A suction source such as a syringe 26 is connected to tubular section 18 upstream or downstream of filter 20. Suction source or syringe 26 is selectively operable to exert an auxiliary force on any clot particles which become stuck in the thrombectomy device upstream of filter screen 20. A three-way valve 28 is provided to alternatively connect (1) syringe 26 to inlet port element 10, (2) syringe 26 to outlet port element 14, or (3) the inlet and outlet port elements 10 and 14 of the tubular device to one another. During normal operation, where the natural pressure differential between the upstream blood vessel and the downstream blood vessel provides the motive force for clot extraction, the third configuration of three-way valve 28 is used. When a thrombus particle becomes lodged in the flow path upstream of filter 20 and particularly in inlet port element 10, three-way valve 28 is operated to connect syringe 26 to inlet port element 10 and to block communication between inlet port element 10 and outlet port element 14. Syringe 26 is then actuated to apply an extraction force to the lodged clot material. Subsequently, three-way valve 28 is manipulated to connect syringe 26 to outlet port element 14 while the flow path between inlet port element 10 and outlet port element 14 remains closed. Blood removed from the flow path during the suction procedure is then immediately conveyed back to the patient's vascular system via outlet port element 14. After clearance of the flow path, three-way valve 28 is operated to restore communication between inlet port element 10 and outlet port element 14.

Instead of three-way valve 28, a pair of automatically functioning one-way valves 30 and 32 may be provided. This arrangement may be particularly useful to ensure that no inadvertent backflow of already trapped clot to the native circulation takes place.

In order to enable or facilitate the guiding of clot material to inlet end 12, a first inflatable balloon 34 in the form of a cuff is provided on inlet port element 10 at inlet end 12 thereof, while a second inflatable balloon 36 is provided at the end of a catheter 38 inserted through cutter head 24. (Balloon 36 may alternatively be an integral part of spoon-like cutter head 24 so that cutter member 22 performs dual functions of cutting clot and blocking blood flow.) Whether one balloon or the other is used depends on the direction of blood flow relative to the upstream section 10, i.e., whether upstream section is inserted against or with the flow of blood. Where inlet port element 10 is inserted against the flow of blood, balloon 34 is inflated while balloon 36 is either not deployed or maintained in an unexpanded configuration. Where inlet port element 10 is inserted in the direction of blood flow, balloon 36 is inflated while balloon 34 is kept in a deflated condition.

An ultrasonic sensor 40 with an electroacoustic sensor (speaker) 42 is provided for sensing fluid flow through middle section 18, particularly downstream of filter screen 20. An interruption in blood flow at that point will signal the operator that syringe 26 must be used to clear out any stuck clot material or that cutter member 22 must be used to carve up a large clot mass which is blocking inlet end 12. It is to be noted that the function of syringe 26, to draw and push back fluid in a piston-like action, can be performed by other, equivalent mechanisms such as a circumferential diaphragm pump or a roller pump.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that the thrombectomy device described herein may be connected between virtually any two points in a patient's vascular system, regardless of the relative pressures at the two points. In particular, the thrombectomy device may be connected at an inlet end and an outlet end to the same blood vessel, preferably at interspaced points. The inlet and outlet tubes in this case may be mutually coaxial, for instance, thereby requiring but a single insertion point. In this case, the annular, outer flow path is preferably for returning blood to the vascular system of the patient. The outer flow path may be enclosed or defined by an introducer sheath, with the returning blood being guided into the sheath through a side port thereof.

If the thrombectomy device is connected between a low pressure blood vessel at an upstream end and a high pressure blood vessel at a downstream end, syringe 26 is used to move the blood and clot material through the thrombectomy device in opposition to the natural vascular pressure differential.

The thrombectomy device may be used with clot cutting or macerating devices other than cutter member 22. Where such a clot cutting or macerating instrument utilizes suction to aspirate severed clot pieces, inlet port element 10 may be connected to the suction channel of the instrument.

Accordingly, it is to be understood that the drawings and descriptions herein are proffered by way of example to facilitate comprehension of the invention and should not be construed to limit the scope thereof.

What is claimed is:

1. A thrombectomy device comprising:
    a tubular member defining a flow path;
    a clot filter disposed in said tubular member and extending transversely to said flow path for removing clot material from blood flowing along said flow path;
    at least one port element on said tubular member for coupling an inlet end of said tubular member to a blood vessel wherein clot material is located and
    for coupling an outlet end of said tubular member to a patient's vascular system including said blood vessel; and
    a cutter element operatively connected to said tubular member so as to be at least partially insertable into said blood vessel for severing clot pieces from a clot mass inside said blood vessel.

2. The device defined in claim 1, further comprising a selectively operable clot clearance component operatively connected to said tubular member for exerting a force on stuck clot material, said force tending to move said clot material along said flow path to said filter.

3. The device defined in claim 2 wherein said clot clearance component includes a suction device.

4. The device defined in claim 3 wherein said port element is one of a first port element and a second port element on said tubular member, said first port element coupling said inlet end of said tubular member to the blood vessel wherein clot material is located, said second port element coupling said outlet end of said tubular member to the patient's vascular system, said clot clearance component further including a three-way valve element operable in first configuration to couple said suction device to said first port element, in a second configuration to couple said suction device to said second port element, and in a third configuration to couple said first port element and said second port element to one another.

5. The device defined in claim 3 wherein said suction device is a piston-type device.

6. The device defined in claim 2, further comprising an inflatable balloon operatively connected to said tubular member and disposable in said blood vessel for blocking flow along said blood vessel to thereby force blood and clot material towards said inlet end of said tubular member.

7. The device defined in claim 6 wherein aid balloon is attached to a tube inserted through said port element.

8. The device defined in claim 1, further comprising an inflatable balloon operatively connected to said tubular member for blocking flow along said blood vessel to thereby force blood and clot material toward said inlet end of said tubular member.

9. The device defined in claim 8 wherein said balloon is attached to a tube inserted through said port element.

10. A method for performing a thrombectomy comprising:
    connecting an inlet end of a tubular member to a blood vessel of a patient, said blood vessel containing clot material;
    connecting an outlet end of said tubular member to a vascular system of the patient, said blood vessel being part of said vascular system;
    guiding blood from said blood vessel through said tubular member to said vascular system;
    capturing, by a filter member disposed in said tubular member, clot material carried with said blood from said blood vessel; and
    operating a cutter element to sever clot pieces from a clot mass inside said blood vessel.

11. The method defined in claim 10, further comprising exerting a force on clot material stuck along a flow path between said blood vessel and said filter member to thereby move the stuck clot material along said flow path to said filter.

12. The method defined in claim 11 wherein the exerting of said force includes applying suction.

13. The method defined in claim 12, further comprising closing communication between said blood vessel and said vascular system through said tubular member prior to the exerting of said force.

14. The method defined in claim 13 wherein the closing of communication includes operating a three-way valve.

15. The method defined in claim 12 wherein the applying of suction includes operating a piston-type device.

16. The method defined in claim 10, further comprising inflating a balloon inside said blood vessel upon connection of said inlet end to said blood vessel and said outlet end to said vascular system, thereby blocking flow of blood along said blood vessel and forcing blood and clot material into said inlet end.

17. The method defined in claim 10 wherein said blood vessel is a first blood vessel of the patient's vascular system, said outlet end of said tubular member being connected to a second blood vessel of the patient, said second blood vessel having a lower blood pressure than said first blood vessel, whereby a pressure differential between said first blood vessel and said second blood vessel exerts a force tending to move said clot material through said tubular member to said filter.

18. A thrombectomy device comprising:
    a tubular member defining a flow path;

a clot filter disposed in said tubular member and extending transversely to said flow path for removing clot material from blood flowing along said flow path;

at least one port element on said tubular member for coupling an inlet end of said tubular member to a blood vessel wherein clot material is located and for coupling an outlet end of said tubular member to a patient's vascular system including said blood vessel;

a valve element connected to and disposed along said tubular member for controlling fluid flow therethrough;

a suction device operatively connected to said tubular member, said valve element being operable in a first configuration to enable said suction device to draw clot and blood from said blood vessel and in a second configuration to enable said suction device to return blood to the patient's vascular system; and a cutter element operatively connected to said tubular member so as to be at least partially insertable into said blood vessel for severing clot pieces from a clot mass inside said blood vessel.

19. The device defined in claim 18 wherein said suction device and said valve element cooperate in said first configuration of said valve element to exert a force on clot material stuck in one of said tubular member and said first port element, said force tending to move said clot material along said flow path to said filter.

20. The device defined in claim 19 wherein said port element is an inlet port element at said inlet end of said tubular member, further comprising an outlet port element at an outlet end of said tubular member, said valve being operable in said first configuration to couple said suction device to said inlet port element, in said second configuration to couple said suction device to said outlet port element, and in a third configuration to couple said inlet port element and said outlet port element to one another.

* * * * *